US008912512B1

(12) United States Patent
Langoju et al.

(10) Patent No.: US 8,912,512 B1
(45) Date of Patent: Dec. 16, 2014

(54) SYSTEM AND METHOD FOR OPTICAL BIOPSY TISSUE CHARACTERIZATION

(71) Applicant: General Electric Company, Schenectady, NY (US)

(72) Inventors: Rajesh Veera Venkata Lakshmi Langoju, Bangalore (IN); Abhijit Vishwas Patil, Bangalore (IN); Sridhar Dasaratha, Bangalore (IN); Vignesh Thirukazhukundram Subrahmaniam, Bangalore (IN); Dmitry Vladimirovich Dylov, Clifton Park, NY (US); Siavash Yazdanfar, Niskayuna, NY (US); Stephen B. Solomon, New York, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 13/927,543

(22) Filed: Jun. 26, 2013

(51) Int. Cl.
G01N 21/64 (2006.01)

(52) U.S. Cl.
CPC .................................. *G01N 21/6486* (2013.01)
USPC ....................................................... 250/459.1

(58) Field of Classification Search
CPC . C12Q 1/6881; G01N 33/57484; G06F 19/24
USPC ....................................................... 250/459.1
See application file for complete search history.

(56) References Cited

U.S. PATENT DOCUMENTS

| 5,991,653 | A | * | 11/1999 | Richards-Kortum et al. | 600/475 |
| 7,376,456 | B2 | | 5/2008 | Marshik-Geurts et al. | |
| 8,224,426 | B2 | | 7/2012 | Lilge et al. | |
| 2005/0171923 | A1 | | 8/2005 | Kiiveri et al. | |
| 2005/0176053 | A1 | | 8/2005 | Malmros et al. | |
| 2008/0194969 | A1 | | 8/2008 | Werahera et al. | |
| 2009/0270702 | A1 | | 10/2009 | Zeng et al. | |
| 2011/0112435 | A1 | | 5/2011 | Ramanujam et al. | |
| 2012/0245473 | A1 | | 9/2012 | Mycek et al. | |

FOREIGN PATENT DOCUMENTS

WO 2012143816 A1 10/2012

OTHER PUBLICATIONS

Richards-Kortum et al., "Quantitative Optical Spectroscopy for Tissue Diagnosis", Physical Chemistry, vol. 47, 1996; 52 Pages.
Skala et al., "Investigation of Fiber-Optic Probe Designs for Optical Spectroscopic Diagnosis of Epithelial Pre-Cancers", Lasers in Surgery and Medicine, pp. 25-38, vol. 34, Issue 1, Jan. 2004.

(Continued)

*Primary Examiner* — Kiho Kim
(74) *Attorney, Agent, or Firm* — Eileen B. Gallagher

(57) ABSTRACT

A method for classifying a tissue sample of a biopsy specimen into one of a plurality of classes is presented. The method includes receiving a light from at least one location of the tissue sample including a plurality of chromophores, wherein the received light comprises at least one of an attenuated illumination light and a re-emitted light. The method further includes processing a spectrum of the received light to determine a feature for each of the chromophores in the at least one location of the tissue sample. In addition, the method includes estimating a Z-score for each of the chromophores based on the determined feature. Also, the method includes classifying the tissue sample into one of the plurality of classes based on the estimated Z-score for each of the chromophores.

24 Claims, 8 Drawing Sheets

(56) References Cited

OTHER PUBLICATIONS

Bard et al., "Optical Spectroscopy for the Classification of Malignant Lesions of the Bronchial Tree", Chest Journal, vol. 129, Issue 4, Apr. 2006; 7 Pages.

Ramanujam, "Fluorescence Spectroscopy in Vivo", Encyclopedia of Analytical Chemistry, pp. 20-56, Sep. 15, 2006.

Skala et al., "Comparison of a Physical Model and Principal Component Analysis for the Diagnosis of Epithelial Neoplasias in Vivo using Diffuse Reflectance Spectroscopy", Optics Express, pp. 7863-7875, vol. 15, Issue 12, 2007.

Zhu et al., "Diagnosis of Breast Cancer using Fluorescence and Diffuse Reflectance Spectroscopy: a Monte-Carlo-Model-based Approach", Journal of Biomedical Optics, vol. 13, Issue 3, May 30, 2008.

Palmer et al., "Quantitative Diffuse Reflectance and Flurescence Spectroscopy: A Tool to Monitor Tumor Physiology in Vivo", Journal of Biomedical Optics, vol. 14, Issue 2, Apr. 22, 2009.

Teh et al., "Near-Infrared Raman Spectroscopy for Early Diagnosis and Typing of Adenocarcinoma in the Stomach", British Journal of Surgery, pp. 550-557, vol. 97, Issue 4, Apr. 2010.

\* cited by examiner

SYSTEM AND METHOD FOR OPTICAL BIOPSY TISSUE CHARACTERIZATION

CROSS-REFERENCE TO RELATED APPLICATIONS

This application is related to U.S. patent application Ser. No. 13/927,807 entitled "System and Method for Holding a Biopsy Collecting Device" filed concurrently and U.S. patent application Ser. No. 13/927,683 entitled "System and Method for Aligning a Biopsy Collecting Device" filed concurrently, the entire disclosures of both are incorporated herein by reference.

BACKGROUND

Embodiments of the present disclosure relate generally to optical spectroscopy, and more particularly to a system and a method for classifying tissue using optical spectroscopy.

In many fields of medicine, tissue classification is widely used to aid diagnosis in a patient. For example, when a patient presents with a suspicious deep tissue lesion, such as those identified during a diagnostic CT scan, the typical workup includes tissue classification to assist in diagnosis and stratify patients for further testing.

Among the existing techniques, core needle biopsy (CNB) is increasingly used as a minimally invasive method to acquire a representative sample of a deep tissue lesion. Typically in CNB, needle intervention is used for taking tissue biopsies and submitting it to pathology to determine a diagnosis. Compared to surgical or excisional biopsy, CNB procedure is less invasive, less expensive, faster, minimizes deformity, leaves little or no scarring and requires a shorter time for recovery. Also, CNB may obviate the need for surgery in a patient with benign lesions and also reduce the number of surgical procedures performed in the patient.

In general, the CNB is a common procedure used to obtain a biopsy specimen that includes a physical sample of a tissue site. Further, the biopsy specimen may be analyzed in a pathology laboratory using histopathological techniques to determine whether the tissue sample is cancerous. However, one of the problems in CNB is that approximately 15-20% of biopsy specimens/samples are non-diagnostic, which yields in too little tissue for a definitive diagnosis. As a result, in some cases, the CNB procedure may be repeated to obtain a viable amount of biopsy specimen/sample from the patient, which may create further complications to the patient. For example, piercing the needle repeatedly into lungs to obtain the biopsy specimen may result in a collapsed lung.

Moreover, the amount of diagnostic tissue in the biopsy specimen may limit the number and types of tests available to the pathologist several days following the biopsy procedure, potentially resulting in a delayed diagnosis and increased risk to the patient. Since the advent of new molecular pathology tests requires a larger amount of viable cancer tissue than conventional histopathology, this problem is likely to increase. Thus, there is a need for an improved method and system for quantifying the amount of diagnostic tissue within the excised biopsy specimen.

BRIEF DESCRIPTION

In accordance with one embodiment described herein, a method for classifying a tissue sample of a biopsy specimen into one of a plurality of classes is presented. The method includes receiving a light from at least one location of the tissue sample including a plurality of chromophores, wherein the received light comprises at least an attenuated illumination light and a re-emitted light. The method further includes processing a spectrum of the received light to determine a feature for each of the chromophores in the at least one location of the tissue sample. In addition, the method includes estimating a Z-score for each of the chromophores based on the determined feature. Also, the method includes classifying the tissue sample into one of the plurality of classes based on the estimated Z-score for each of the chromophores.

In accordance with a further aspect of the present disclosure, a device for classifying a tissue sample of a biopsy specimen into one of a plurality of classes is presented. The device includes a detecting unit configured to receive a light from at least one location of the tissue sample comprising a plurality of chromophores, wherein the received light comprises at least an attenuated illumination light and a re-emitted light. Also, the device includes a processing unit coupled to the detecting unit and configured to process a spectrum of the received light to determine a feature for each of the chromophores in the at least one location of the tissue sample, estimate a Z-score for each of the chromophores based on the determined feature, and classify the tissue sample into one of the plurality of classes based on the estimated Z-score for each of the chromophores.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

As will be described in detail hereinafter, various embodiments of exemplary structures and methods for diagnosing tissue are presented. By employing the methods and the various embodiments of the system described hereinafter, the amount of diagnostic tissue in an excised biopsy specimen is determined without removing the biopsy specimen from a biopsy needle.

Figure 1:
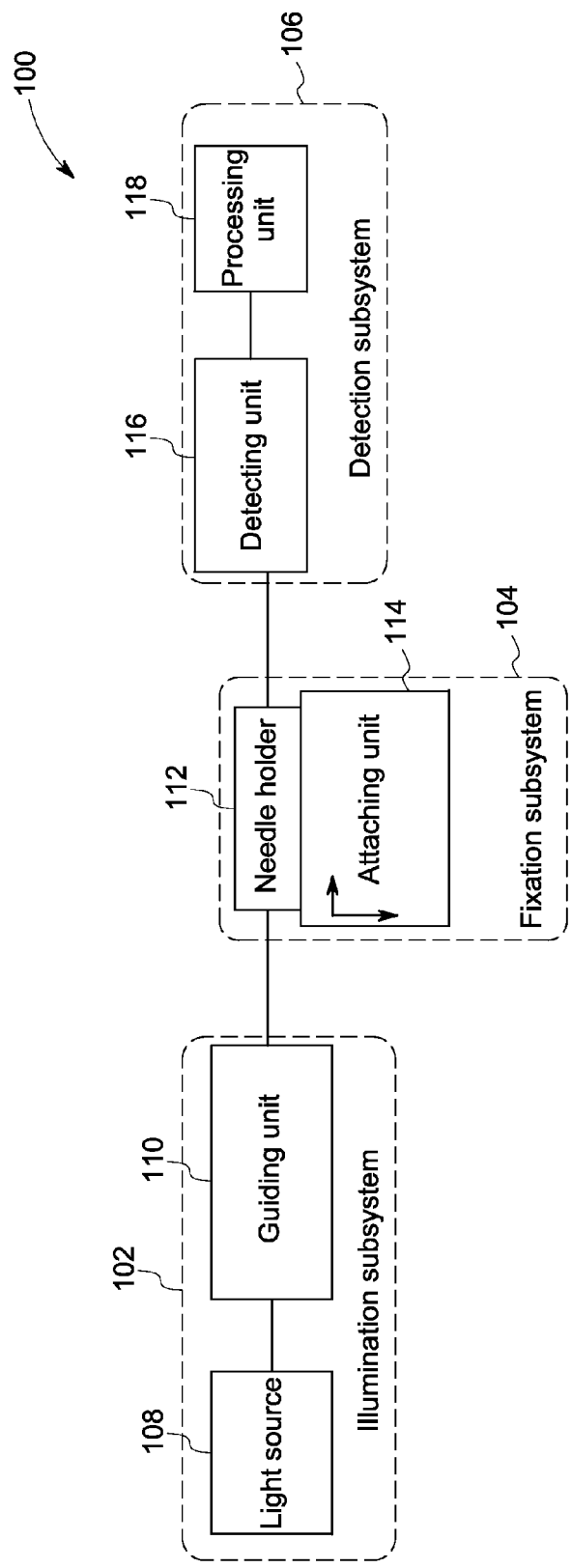
FIG. 1 is a block diagram of a spectroscopy system for diagnosing tissue in a biopsy specimen, in accordance with aspects of the present disclosure.

Turning now to the drawings, and referring to FIG. 1, a spectroscopy system for diagnosing tissue, in accordance with aspects of the present disclosure, is depicted. The spectroscopy system 100 may be used to determine an amount of diagnostic tissue present in an excised biopsy specimen. More specifically, the biopsy specimen may include one or more tissue samples that are classified into one or more tissue classes, which in turn aids in determining a quantity and/or a quality of the diagnostic tissue in the biopsy specimen. In one example, the one or more tissue classes may include a normal tissue class and an abnormal tissue class. The normal tissue class is referred to as a class of tissue samples having no cancerous tissues, such as benign tissue or blood, while the abnormal tissue class is referred to as a class of tissue samples having cancerous tissues, including malignant or necrotic tumor, or other diseased tissue such as fibrosis. Also, the spectroscopy system 100 may be used to characterize the biopsy specimen in a biopsy needle or a biopsy collecting device immediately after excision. It is to be noted that the biopsy specimen may be referred to as a physical sample of a region in a patient. In one example, the biopsy specimen may include at least a normal tissue and/or a cancerous tissue of a patient.

In accordance with one embodiment, the spectroscopy system 100 includes an illumination subsystem 102, a fixation subsystem 104, and a detection subsystem 106. The illumination subsystem 102 is configured to emit an illumination light towards the biopsy specimen. The illumination light may be in a range from about 200 nm to about 1100 nm. As depicted in FIG. 1, the illumination subsystem 102 includes a light source 108 and a guiding unit 110 that is coupled to the light source 108. In one example, the light source 108 may include a deuterium tungsten halogen source that is configured to emit a broadband light towards the biopsy specimen. Further, the guiding unit 110 may include optical fibers and lenses that are used for guiding the emitted illumination light towards the biopsy specimen. In one embodiment, the guiding unit 110 may include a plurality of optical fibers that are used to deliver the emitted illumination light at multiple locations along the biopsy specimen.

In a presently contemplated configuration, the fixation subsystem 104 is configured to position the biopsy specimen across the illumination light that is emitted by the illumination subsystem 102. As depicted in FIG. 1, the fixation subsystem 104 includes a needle holder 112 and an attaching unit 114. The needle holder 112 is configured to hold a biopsy collecting device (not shown in FIG. 1) that comprises the biopsy specimen. Particularly, the biopsy collecting device may include an activator unit and a needle unit. A portion of the needle unit may be pierced into the patient towards a sample/tissue site to obtain the biopsy specimen. Thereafter, the biopsy collecting device may be fastened to the needle holder 112 that provides an interface between the biopsy collecting device and the detection subsystem 106. More specifically, the needle holder 112 may be used for precisely positioning at least the needle unit relative to the illumination light while scanning the biopsy specimen.

In addition, the attaching unit 114 is coupled to the needle holder 104 for positioning the biopsy collecting device at a predetermined position and/or angle in the spectroscopy system 100. For example, the attaching unit 114 may include one or more actuators that are employed for moving the needle holder 112 in a forward or backward direction with respect to an illumination path. Since the needle holder 112 is holding the biopsy collecting device, the movement of needle holder 112 may also move the biopsy specimen across the illumination path. This in turn provides the means for placing the biopsy specimen across the illumination light. Thus, the attaching unit 114 is used for positioning the biopsy collecting device at the predetermined position/angle so that the illumination light may scan the biopsy specimen present in the needle unit. The aspect of positioning the biopsy specimen across the illumination light is explained in greater detail with reference to FIG. 5.

Furthermore, the detection subsystem 106 is coupled to the fixation subsystem 104 and aligned with the illumination subsystem 102 for determining the diagnostic tissue in the biopsy specimen. The detection modality may be based on a variety of optical detection methods including but not limited to, diffuse optical spectroscopy, fluorescence spectroscopy, optical coherence tomography, Raman spectroscopy, or combinations thereof. In one exemplary embodiment, the detection subsystem uses diffuse optical spectroscopy for determining the diagnostic tissue in the biopsy specimen.

As depicted in FIG. 1, the detection subsystem 106 includes a detecting unit 116 and a processing unit 118. The detecting unit 116 is used for generating an electrical signal corresponding to a light comprising an attenuated illumination light and/or a re-emitted light from the biopsy specimen. Particularly, the detecting unit 116 includes one or more optical detectors that are aligned with the illumination path so as to receive the illumination light emitted by the illumination subsystem 102 and the light re-emitted from the biopsy specimen. The received light may be attenuated by one or more molecules in the biopsy specimen. More specifically, the molecules in the biopsy specimen may absorb, scatter, and/or attenuate the illumination light while passing through the biopsy specimen. This in turn causes transmission losses at various wavelengths in spectra of the illumination light. It is to be noted that the illumination light with such transmission losses may also be referred to as the attenuated illumination light. In one embodiment, the received light may be comprised of attenuated illumination light with transmission losses at various wavelengths, which may include information on the absorbance of molecules comprising the tissue, the inhomogeneity of the tissue refractive index, and the secondary light re-emitted by molecules due to fluorescence and/or Raman scattering phenomena. Also, it may be noted that the received and emitted illumination light paths may be in more than one direction. In one example, the illumination path may be orthogonal or at an oblique angle, e.g., 45 degrees, to the detected light path. Further, the detected light is converted to a corresponding electrical signal.

In addition, the processing unit 118 that is coupled to the detecting unit 116 may receive the electrical signal representing the received light. Further, the received electrical signal is processed to determine the diagnostic tissue in the biopsy specimen. Particularly, the spectrum of the received light may be analyzed to classify the tissue sample into at least one of the normal tissue class and the abnormal tissue class. Thereafter, the classified tissue sample is used to determine the quantity and the quality of the diagnostic tissue in the biopsy specimen. The aspect of processing the spectrum of the received light is explained in greater detail with reference to FIG. 6. After completion of the analysis, the biopsy specimen may be removed from the biopsy collecting device and transferred to a tissue fixation medium, e.g., formalin, for pathology. Thus, by using the exemplary spectroscopy system 100, the diagnostic tissue within the excised biopsy specimen is determined without removing the biopsy specimen from the biopsy needle or the biopsy collecting device. Also, conducting analysis directly in the biopsy needle or the biopsy collecting device may minimize stress on the biopsy specimen/sample and impact on workflow, prior to transferring the biopsy specimen/sample for histopathology or cytopathology.

Figure 2:
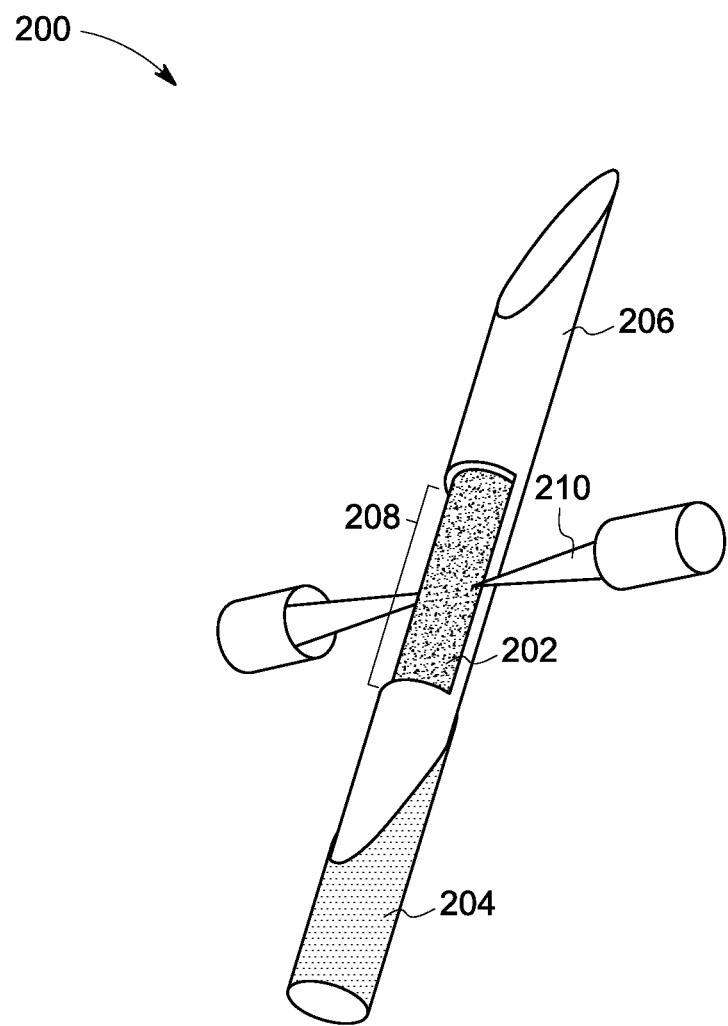
FIG. 2 is an illustration of a needle unit comprising a biopsy specimen, in accordance with aspects of the present disclosure.

Referring to FIG. 2, an illustration of a needle unit comprising a biopsy specimen, in accordance with aspects of the present disclosure, is depicted. For ease of understanding, the needle unit 200 is described with reference to the components of FIG. 1. It is to be noted that the needle unit 200 may be considered as a part or a component of the biopsy collecting device. As appreciated, the needle unit 200 may be pierced into a patient towards a desired tissue or sample site to obtain the biopsy specimen 202 from the patient. As depicted in FIG. 2, the needle unit 200 includes an outer sheath, which is known as a cannula 204 and an inner sheath, which is known as a stylet 206. The stylet 206 may be configured to extend or retract from the cannula 204. Further, the stylet 206 may have a collection area 208 for collecting the biopsy specimen 202 from the patient.

Moreover, upon collecting the biopsy specimen 202 from the patient, the biopsy collecting device having the needle unit 200 may be fastened to a needle holder 112. Particularly, the cannula 204 may be fastened to the needle holder 112, while the stylet 206 may be extended or retracted from the cannula 204. In one embodiment, the stylet 206 may be extended or retracted to position the biopsy specimen 202 across an illumination path 210. Also, in another embodiment, the stylet 206 may be extended or retracted so that the illumination light may scan the biopsy specimen 202 at multiple locations. The aspect of fastening the needle unit 200 and scanning the biopsy specimen 202 is explained in greater detail with reference to FIG. 4.

Figure 3:
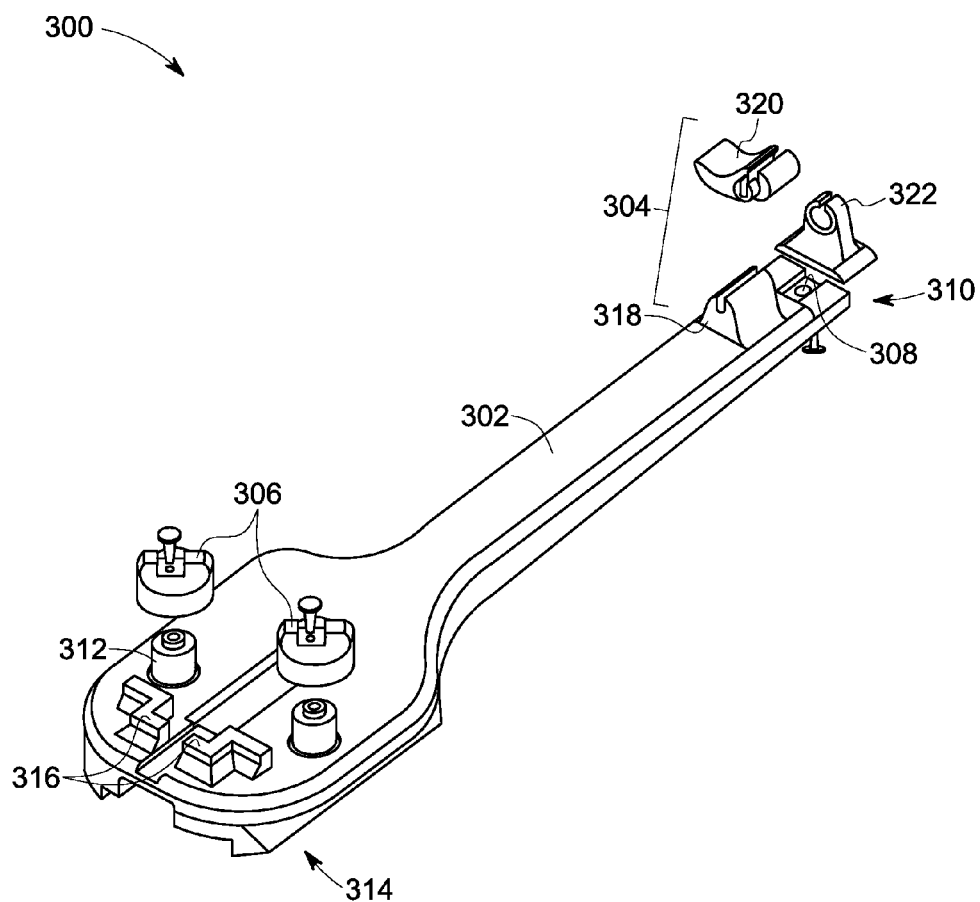
FIG. 3 is an illustration of an exploded view of a needle holder, in accordance with aspects of the present disclosure.

FIG. 3 illustrates an exploded view of an exemplary needle holder, in accordance with aspects of the present disclosure. Reference numeral 300 may be representative of the needle holder 112 of FIG. 1. The needle holder 300 includes a base unit 302, a fastening unit 304, and a holding unit 306. The base unit 302 may act as a support platform for receiving a biopsy collecting device 402. In addition, the base unit 302 includes a couple of apertures 308 at a first end 310 of the base unit 302 and a couple of protruding members 312 at a second end 314 of the base unit 302. The apertures 308 are used for coupling the fastening unit 304 to the base unit 302. Particularly, the fastening unit 304 includes a first sub-unit 318, a second sub-unit 320, and a third sub-unit 322. The first sub-unit 318 and the third sub-unit 322 may be coupled to the base unit 302 by inserting a screw or other fastening device in each of the corresponding apertures 308 of the base unit 302 and into the respective sub-units 318, 322, as depicted in FIG. 3. In addition, the second sub-unit 320 may be coupled to the first sub-unit 318 and the third sub-unit 322.

In a similar manner, the protruding members 312 at the second end 314 are used for coupling the holding unit 306 to the base unit 302. Particularly, the holding unit 306 may include one or more knobs that are coupled to protruding members 312 of the base unit 302. In one example, a screw or other fastening device may be inserted through the knob and into the protruding member 312 of the base unit 302, as depicted in FIG. 3. In addition, the base unit 302 includes one or more wedges 316 that may lock with the walls of the biopsy collecting device.

Figure 4:
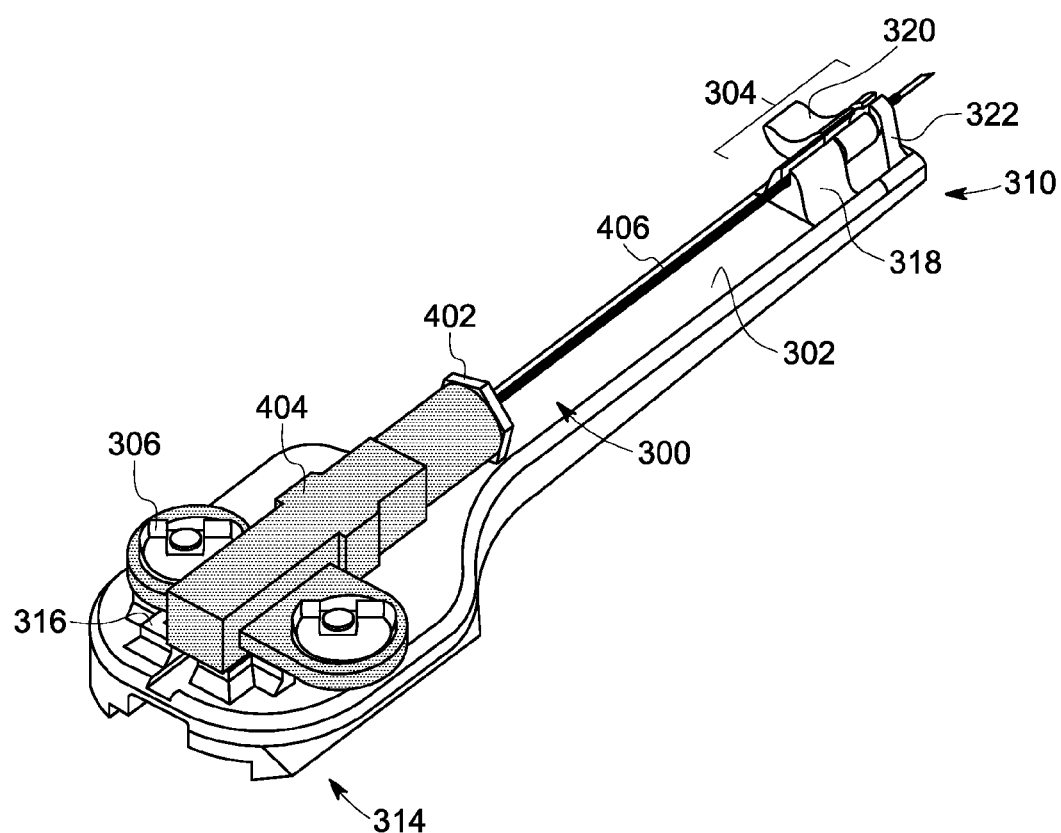
FIG. 4 is an illustration of an apparatus holding a biopsy collecting device, in accordance with aspects of the present disclosure.

Referring to FIG. 4, a needle holder having a biopsy collecting device, in accordance with aspects of the present disclosure, is depicted. The biopsy collecting 402 device is used to obtain a biopsy specimen from a patient, and then it is snapped into the needle holder 300. As depicted in FIG. 4, the biopsy collecting device 402 includes an activator unit 404 and a needle unit 406. The needle unit 406 is representative of the needle unit 200 of FIG. 2. The needle unit 406 may include a cannula 204 and a stylet 206. Further, the activator unit 404 that is coupled to a rear end of the needle unit 406 is configured to extend or retract the stylet 206 relative to the cannula 204.

Furthermore, the fastening unit 304 is used for fastening a portion of the needle unit 406 to the base unit 302. Particularly, the fastening unit 304 may be used to lock the cannula 204 of the needle unit 406 with the base unit 302. In the embodiment of FIG. 4, the fastening unit 304 includes a first sub-unit 318, a second sub-unit 320, and a third sub-unit 322. The first sub-unit 318 and the third sub-unit 322 include a channel or u-shaped grove on a top surface of the first sub-unit 318. This channel may collect the portion of the cannula 204 when the biopsy sample collecting device 402 is positioned on the base unit. Further, the second sub-unit 320 is configured to secure or fasten the portion of the cannula 204 within the channel of the first and third sub-units 318, 322. Particularly, the second sub-unit 320 comprises a clamp that is coupled between the first and third sub-units 318, 322. The clamp includes a u-shaped groove on the top-surface that is aligned with the channel of the first and third sub-units 318, 322. Further, when the needle unit 406 is pressed on the base unit 302, the channel in the first and third sub-units 318, 322 and the u-shaped groove in the second sub-unit 320 receive the portion of the cannula 204. Thereafter, the clamp is rotated over the cannula 204 to fasten the portion of the cannula within the channel of the first and third sub-units 318, 322. Also, the cannula 204 is fastened to the base unit in such a way that the stylet 206 of the needle unit 406 is projected over the first end 310 of the base unit 302, as depicted in FIG. 4.

In a presently contemplated configuration, the holding unit 306 is configured to fasten the activator unit 404 of the biopsy collecting device 402 to the base unit 302. Particularly, the holding unit 306 includes one or more knobs that are disposed on the base unit 302 and configured to lock the activator unit 404 to the base unit 302. In one embodiment, the knobs are used to fasten with a corresponding ring/aperture of the activator unit 404, as depicted in FIG. 4.

In an alternate embodiment, the biopsy collecting device 402 may be directly interfaced to the base unit 302. Particularly, the activator unit 404 may include a tab that snaps into the base unit 302 directly, and the fastening unit 304 may be used to hold the needle unit 406. Also, in another embodiment, the fastening unit 304 may hold the needle unit 406 irrespective of the activator unit 404 coupled to the base unit 302. It may be noted that the biopsy collecting device 402 may be coupled to the needle holder 300 by using any fastening structure, and is not limited to the structure shown in FIG. 4.

Figure 10:
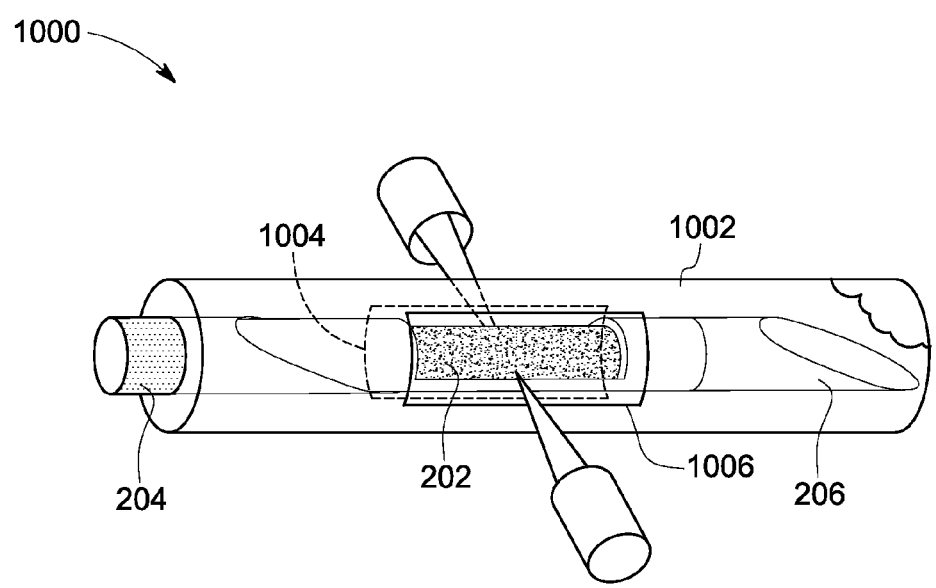
FIG. 10 is an illustration of a portion of a needle unit enclosed in a container, in accordance with aspects of the present disclosure.

Furthermore, in one embodiment, the needle holder 300 may include a container 1000 that further includes a fixative 1002, such as formalin, as depicted in FIG. 10. Further, at least a portion of the biopsy collecting device 402 is placed inside the container 1000 in such a way that the stylet 206 comprising the biopsy specimen 202 may be immersed in the fixative 1002. Particularly, the biopsy specimen 202 is immersed in the fixative to prevent the biopsy specimen 202 from being exposing to air or other contaminants. Also, the container is provided with one or more windows 1004, 1006, particularly at the location where the biopsy specimen 202 is positioned. These windows 1004, 1006 allow optical access to the biopsy specimen 202, for the illumination light to reach and be collected from the biopsy specimen 202 that is placed in the needle unit 406.

Figure 5:
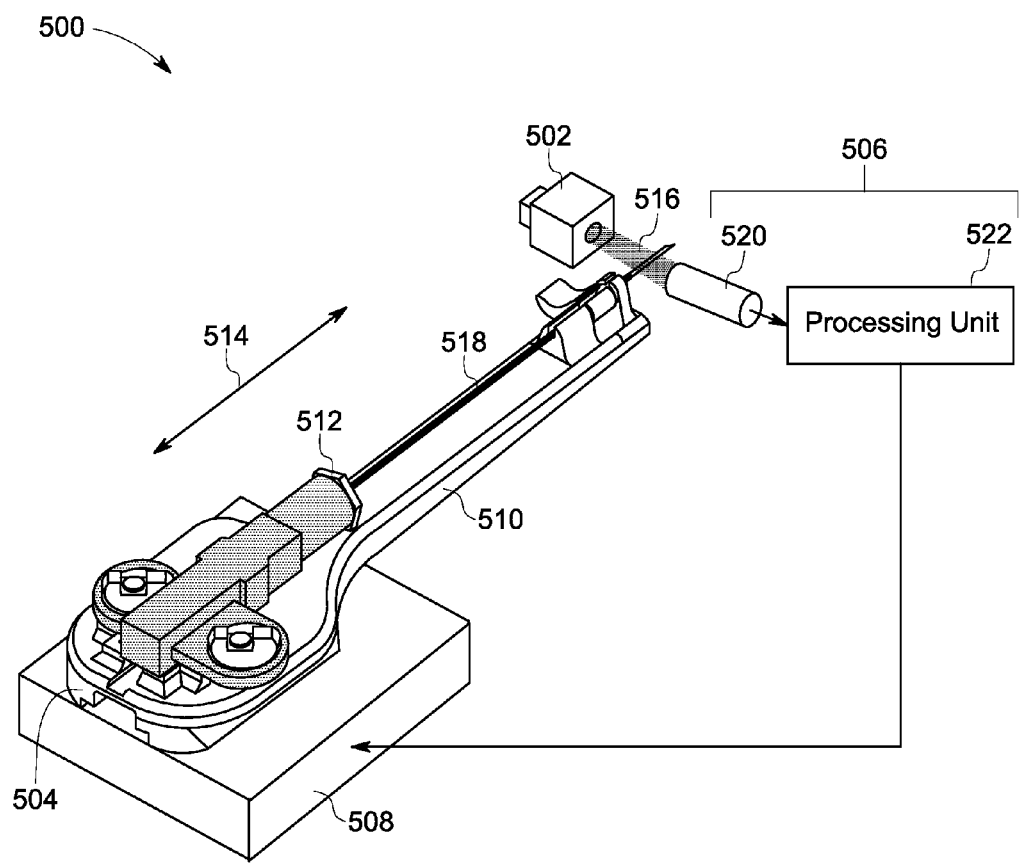
FIG. 5 is a spectroscopy system automatically aligning a biopsy specimen across an illumination light, in accordance with aspects of the present disclosure.

Referring to FIG. 5, a spectroscopy system automatically aligning a biopsy specimen across an illumination light, in accordance with aspects of the present disclosure, is depicted. For ease of understanding of the present disclosure, the spectroscopy system 500 is described with reference to the components of FIGS. 1-4. Reference numeral 502 may be representative of the illumination subsystem 102, reference numeral 504 may be representative of the fixation subsystem 104, and reference numeral 506 may be representative of the detection subsystem 106 of FIG. 1. The illumination subsystem 502 may include a light source 108 that is configured to emit an illumination light and a guiding unit 110 to guide the emitted illumination light towards the detection sub-system 506, as depicted in FIG. 5. In a similar manner, the detection sub-system 506 may be used for receiving the illumination light and processing it to determine the diagnostic tissue in the biopsy specimen. As such the sub-system further comprises a processing unit 522.

In a presently contemplated configuration, the fixation subsystem 504 includes an attaching unit 508 that is coupled to a needle holder 510. The needle holder 510 may be representative of the needle holder 300 of FIG. 3. The needle holder 510 may be used to hold a biopsy collecting device 512 having the biopsy specimen. Furthermore, the needle holder 510 is mounted on the attaching unit 508 that is configured to position the needle holder 510 at a predetermined position/angle in the spectroscopy system 500. In one example, the attaching unit 508 may include one or more actuators that may receive control signals from the detection subsystem 506 and accordingly move the needle holder 510 in a forward or backward direction 514 relative to an illumination path 516.

In an exemplary embodiment, the biopsy specimen is automatically aligned to a predetermined position/angle in the spectroscopy system 500. Particularly, a portion of a needle unit 518 of the biopsy collecting device 512 is first placed between the illumination subsystem 502 and the detection subsystem 506. Further, the illumination light that is passing through or above the needle unit 518 is processed by the detection subsystem 506 to determine a current position of the needle unit 518. In one example, if the illumination light is hitting a metal portion, such as a stylet 206 or a cannula 204 of the needle unit 518, the illumination light may not be received by the detection subsystem 506. Thus, there will be a substantial amount of signal drop or the signal may not be received by the detection subsystem 506. In another example, if the illumination light is passing through air above the needle unit 518, the illumination light may not undergo attenuation or transmission losses, and thus, there will be no signal drop at the detection subsystem 506. Based on the signal strength and/or the transmission losses in the received signal, the detection subsystem 506 may determine the current position of the needle unit 518.

Upon determining the current position of the needle unit 518, the detection subsystem 506 may send one or more control signals to the attaching unit 508 to progressively move the needle unit 518 in a forward or backward direction 514 until the biopsy specimen is placed at the predetermined position/angle across the illumination path 516. In one example, if a tip of the needle unit 518, particularly the tip of the stylet 206 is in the illumination path 516, the processing unit 522 may send one or more controls signals to the attaching unit 508 to move the biopsy collecting device 512 in a forward direction relative to the illumination path 516. These control signals are provided to the attaching unit 508 until the biopsy specimen in the collection area of the stylet 206 is placed across the illumination path 516.

After placing or positioning the biopsy specimen across the illumination path 516, the illumination light may interact with the biopsy specimen and it may interact with or be attenuated by molecules or chromophores in the biopsy specimen. The resulting re-emitted or attenuated illumination light may be further received by a detecting unit 520 of the detection subsystem 506. In one embodiment, the needle unit 518 may be moved in a forward or backward direction 514 so as to pass the illumination light through multiple locations of the tissue sample in the biopsy specimen. This in turn helps in obtaining a detected signal resulting from illumination lights that passed through one or more locations of the tissue sample.

Furthermore, the detecting unit 520 may receive a light comprising the attenuated illumination light and/or the re-emitted light, and generates an electrical signal corresponding to the received light. Thereafter, the electrical signal corresponding to the received light is sent to the processing unit 522. Further, the processing unit 522 may analyze the generated electrical signal to diagnose tissue in the biopsy specimen. More specifically, the electrical signal may be processed by using one or more algorithms to determine one or more parameters of the biopsy specimen. The parameters may include, but not limited to, classification, quantity, quality, or other characteristics of diagnostic tissue in the biopsy specimen. The aspect of processing the signal is explained in greater detail with reference to FIG. 6.

Figure 6:
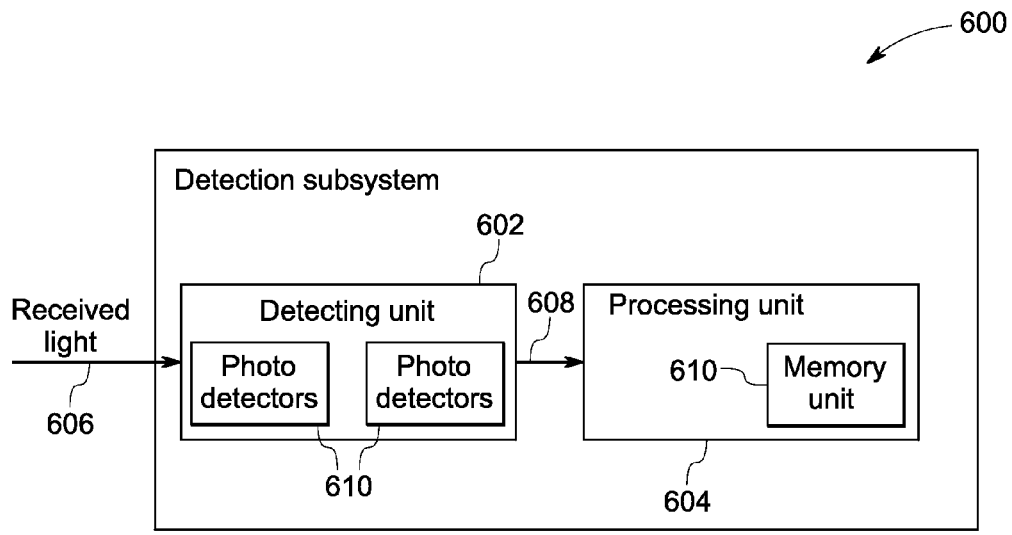
FIG. 6 is a detection subsystem processing a received light to determine the diagnostic tissue, in accordance with aspects of the present disclosure.

Referring to FIG. 6, a detection subsystem processing a received light 606 to determine the diagnostic tissue, in accordance with aspects of the present disclosure, is depicted. The received light 606 may comprise an attenuated illumination light and/or a re-emitted light from the biopsy specimen. Reference numeral 600 may be representative of the detection subsystem 106 of FIG. 1. The detection subsystem 600 includes a detecting unit 602 and a processing unit 604. The detecting unit 602 may be similar to the detecting unit 116 and the processing unit 604 may be similar to the processing unit 118 of FIG. 1.

In a presently contemplated configuration, the detecting unit 602 may be aligned with an illumination subsystem 102 to receive the illumination light emitted from the illumination subsystem 102 and the re-emitted light. The illumination light may pass through a biopsy specimen that is positioned between the illumination subsystem 102 and the detection subsystem 106, 600. Particularly, the illumination light may pass through at least one location of a tissue sample of the biopsy specimen. Also, the illumination light may be attenuated while passing through the tissue sample. In one example, the illumination light may be attenuated when molecules or chromophores in the tissue may absorb or scatter the illumination light. The chromophores may include for example, oxy hemoglobin, deoxy hemoglobin, water, NAD(P)H, FAD, Beta carotene, fat, lipids, collagen, elastin, flavins, or combinations thereof.

As greatly appreciated, the illumination light may interact with the tissue sample in the biopsy specimen and may convey information on the state of the diagnostic tissue. Also, these interactions may yield information for diagnosis at the biochemical, structural, or physiological level of the tissue. In addition, endogenous or exogenous chromophores in the tissue sample may be used for interrogation. The endogenous chromophores such as oxy and de-oxy hemoglobin, water are known to absorb the illumination light 606 in the wavelength region of about 600 nm to about 1000 nm. In this region, tissue scattering is known to dominate over absorption. Additionally, in the UV and near-UV range of the illumination light 606, chromophores such as NAD(P)H, flavins, may provide diagnostic information. Each tissue is known to contain certain chromophores predominantly, and hence analyzing them may convey the absorption characteristics of the tissue.

Furthermore, the detecting unit 602 may include one or more photo detectors 610 that are used for converting the received light 606 to a corresponding electrical signal 608. The electrical signal 608 may represent spectrum of the received light 606. Since the illumination light is attenuated by the biopsy specimen, the spectrum of the received light 606 may include one or more spectra associated with chromophores present in the biopsy specimen. In one example, a tissue sample in the biopsy specimen may contain a mixture of certain chromophores and each chromophore may absorb a particular spectral range of the illuminated light. Further, the converted electrical signal 608 is transmitted to the processing unit 604 that is communicatively coupled to the detecting unit 602.

In an exemplary embodiment, chromophore quantification in the tissue sample may be based on the tissue score that comprises combination of all or some of the chromophores present in a tissue spectrum:

$$\beta = \frac{1}{T_0} \cdot \prod_j p(\lambda_j) \quad (1)$$

Where $\beta$ is referred to as a tissue index that comprises a plurality of features in the tissue spectrum, $T_0$ is proportionality constant and $p(\lambda_j)$ is the contrast of particular spectral feature in the region of wavelength $\lambda_j$. In one embodiment, $p(\lambda_j)$ is defined as the prominence of a spectral peak, which is determined by using equation:

$$p(\lambda_j) = (T_{max} - T_{min})/(T_{max} + T_{min}) \quad (2)$$

Where $T_{max}$ represents the maximum of the received signal measured near the spectral peak of interest and $T_{min}$ represents the minimum of the received signal measured near the spectral peak of interest. Also, in another embodiment, $p(\lambda_j)$ is defined as an integral of the measured spectrum $T(\lambda)$ over a region of interest, which is determined by using equation:

$$p(\lambda_j) = \int_{\lambda_1}^{\lambda_2} T(\lambda) d\lambda \quad (3)$$

Where $\lambda_j = (\lambda_1 + \lambda_2)/2$ is the center of spectral region that extends from wavelengths $\lambda_1$ to $\lambda_2$. In yet another embodiment, $p(\lambda_j)$ is defined as a slope of the spectrum, which is determined by using equation:

$$p(\lambda_j) = \left|\frac{dT(\lambda)}{d\lambda}\right|^{-1} \quad (4)$$

Where $\lambda_j = (\lambda_3 + \lambda_4)/2$ is the center of a spectral region that extends from wavelengths $\lambda_3$ to $\lambda_4$. It may be noted that these wavelengths $\lambda_3$ and $\lambda_4$ may be same as the wavelengths $\lambda_1$ and $\lambda_2$ or different from the wavelengths $\lambda_1$ and $\lambda_2$. Further, $T_0$ is referred to as a normalization constant for the measured spectrum $T(\lambda)$. Also, the wavelength $\lambda_j$ is in a range from about 200 nm to 1100 nm.

Furthermore, the determined tissue index $\beta$ may be used to classify the tissue sample into one of the plurality of classes. Particularly, the tissue sample is classified based on a threshold level of the tissue index $\beta$ between the plurality of classes.

In another exemplary embodiment, the processing unit 604 may initially determine weights of certain chromophores in a known or predetermined normal tissue sample. In one example, the weights are referred to as strength of chromophores in the tissue sample. In a similar manner, weights are determined for the same type of chromophores in a known or predetermined cancerous/abnormal tissue sample. It is to be noted that the known normal tissue sample and the known cancerous/abnormal tissue sample are pre-stored samples, and are not obtained from tissue samples in the current biopsy specimen that is excised from a patient. It may be noted that the pre-stored samples/data may be a collection of data obtained from a variety of pre-analyzed cancer and/or normal tissue samples that have been classified using gene expression differences, morphology, and other parameters useful in diagnosing disease. The data may be stored in a library type of format or accessible data files. In one embodiment, the weights may be determined for some of the commonly found or selected chromophores, such as, but not limited to oxy and deoxy hemoglobin, DNA, FAD, Beta carotene, fat, lipids, and collagen. It may be noted that the weight of the chromophore may be referred to as one of the features of the chromophore.

Moreover, the weights of chromophores in the normal tissue sample may be different from the weights of chromophores in the abnormal tissue sample. Also, these weights may differ with respect to a region in the body where the tissue sample is obtained. For example, the weights of chromophores in a tissue sample of a liver may be different from the weights of chromophores in a tissue sample of a kidney. Furthermore, these determined weights are stored in a memory unit 610 and are used as pre-stored data while processing the current biopsy specimen/tissue sample.

Upon obtaining the weights of chromophores in the known or pre-stored tissue samples, the processing unit 604 may process the actual tissue sample in the excised biopsy specimen to determine weights of corresponding/selected chromophores in the actual tissue sample. Particularly, the processing unit 604 may process the spectrum of the received light to determine the weight for each of the chromophores in at least one location of the tissue sample. The equation relating to the spectrum of the received light and the chromophore spectra is given by a generalized linear model, which is as shown below.

$$P(\lambda) = \sum_{i=1}^{N} w_i S_i(\lambda) + \eta(\lambda) \quad (5)$$

Wherein, $w_i$ represents the weight of the $i^{th}$ chromophore in the tissue sample, $P(\lambda)$ represents the spectrum of the received light, $\{S_i(\lambda)\}$ represents a library spectrum, and $\eta(\lambda)$ accounts for the unknown spectra in the tissue sample. The library spectrum may be the pre-stored data that includes spectrum of each chromophore in the normal tissue sample and the abnormal tissue sample. In one embodiment, the processing unit 604 may determine an optimal linear combination of the pre-stored data that matches with the spectrum of the received light. Further, the determined optimal linear combination of the pre-stored data may be used to estimate the weight for each of the chromophores. In one embodiment, an error in equation (5) may be defined as the difference between the spectrum of the received illumination light and the optimal linear combination of the library spectra or pre-stored data.

Further, the weights of the chromophores may be estimated by minimizing the sum of squares of the error in equation (5) which is shown by the following equation.

$$w_{est} = \arg\min \left\| P(\lambda) - \sum_{i=1}^{N} w_i S_i(\lambda) \right\|^2 \qquad (6)$$

This is a linear least squares problem, where the weights $\{w_i\}$ of each chromophore may be estimated by the below equation.

$$w_{est} = (S^T S)^{-1} S^T P \qquad (7)$$

In one embodiment, the weights of these chromophores are estimated in a least square sense to minimize an error between the pre-stored data and the spectral response of selected chromophores in the tissue sample. Moreover, the key or selected chromophores may be identified from absolute values of $\{w_i^{est}\}$. In addition, the processing unit 604 may determine variance of these weights to overcome variations in optical setup of the spectroscopy system. In one example, the variations in optical set up may include different probe geometry, distance of optical probe from the tissue, variation of intensity of the light source, probe configuration, probe angle, illumination source error, and misalignment of the spectroscopy system 100. The variance of these weights may be determined based on the variance of the error and the covariance of the matrix of the chromophore spectra. In one embodiment, the covariance of the matrix of the chromophore spectra is referred to as a co-variance of the library spectra. Particularly, the variance of the error in equation (7) is determined by using the below equation.

$$\sigma^2 = \text{Var}(P(\lambda)) - \sum_{i=1}^{N} w_i^{est} S_i(\lambda) \qquad (8)$$

Also, the covariance of the matrix of the chromophore spectra is determined by using the below equation.

$$C = [E\{S^T S\}] \qquad (9)$$

Further, the variance of these weights may be determined by using equations (8) and (9), which is represented by the below equation.

$$R = \sigma^2 inv[E\{S^T S\}] \qquad (10)$$

More specifically, the variance of these weights may be determined from the diagonal elements of matrix 'R' in equation (10), which is shown by the below equation.

$$\zeta^i = R_{ii} \qquad (11)$$

Also, in one embodiment, the variance of these determined weights may be referred as the variability of the estimated chromophore concentrations. Furthermore, the processing unit 604 may use the determined weights and variability of the estimated chromophore concentrations to compute Z-scores for each of the chromophores. As used herein Z-score refers to as calculating an uncertainty adjusted representation of the feature or weight for each of the chromophores. Particularly, Z-scores are computed for each of the chromophores by using the equation:

$$Z_i = w_i / \sqrt{\zeta^i} \qquad (12)$$

In one embodiment, the processing unit 604 may determine a standard deviation of the spectrum of the received illumination light. Further, the processing unit 604 may use the standard deviation of the spectrum and the determined weights of the chromophores to estimate the Z-score for each of the chromophores. Also, if the estimated Z-score '$Z_i$' is greater than 2, then it is considered that these weights '$w_i$' are determined with 95% confidence.

Further, the computed Z-scores for each of the chromophores may be used for classifying the tissue sample. More specifically, the processing unit 604 may determine a probabilistic score for the at least one location of the tissue sample based on the estimated Z-score of each of the chromophores in the at least one location of the tissue sample. Furthermore, the above process may be repeated for multiple locations in the tissue sample to determine probabilistic score at each location of the tissue samples. Thereafter, the processing unit 604 may compute an effective probabilistic score for the tissue sample based on the determined probabilistic score for each location of the tissue samples. Further, this effective probabilistic score of the tissue sample may be used to classify the tissue sample as the normal tissue or the abnormal tissue. For example, if the probabilistic score is 60% then the at least one location of the tissue sample may include 60% cancerous/abnormal tissue. In one embodiment, the weight of each chromophore along with its variance may be fed to a Generalized Linear Model (GLM), a classification algorithm, which predicts the probability of tissue sample belonging to a particular class. Thus, by classifying the tissue samples of the biopsy specimen, the processing unit 604 may diagnose the tissue in the biopsy specimen. Also, the processing unit 604 may determine the quantity, the quality, and other characteristics of the diagnostic tissue in the biopsy specimen.

Figure 7:
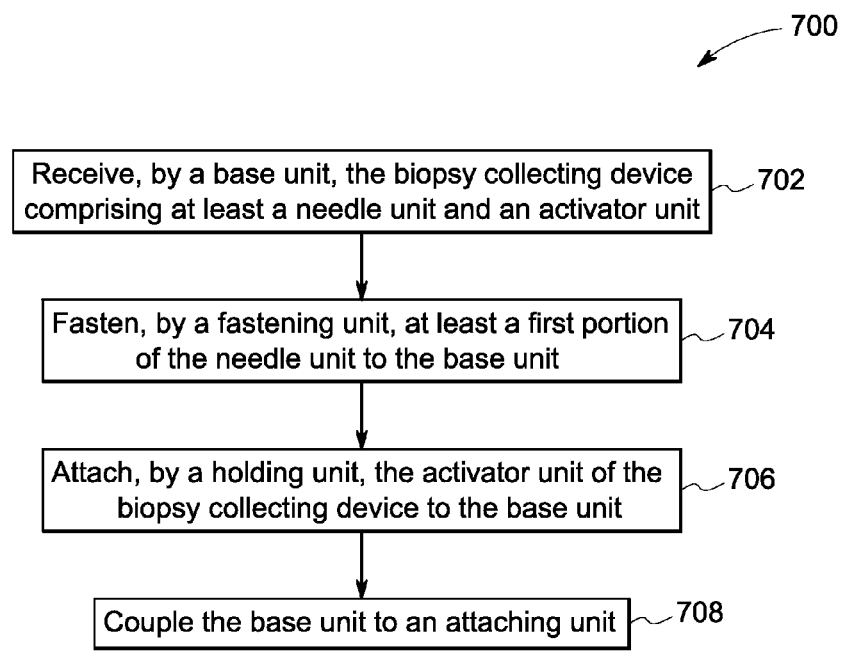
FIG. 7 is a flow chart illustrating a method for holding a biopsy collecting device, in accordance with aspects of the present disclosure.

Referring to FIG. 7, a flow chart illustrating a method for holding a biopsy collecting device, in accordance with aspects of the present disclosure, is depicted. For ease of understanding of the present disclosure, the method is described with reference to the components of FIGS. 1-6. The method begins at step 702, where the biopsy collecting device 402 comprising an activator unit 404 and a needle unit 406 is received by a needle holder 300. Particularly, the needle unit 406 having a stylet 206 and a cannula 204 is pierced into a patient to collect a biopsy specimen from a desired tissue site in the patient. Further, the biopsy collecting device 402 is placed on a base unit 302 of a needle holder 300 for diagnosing tissue in the biopsy specimen.

Subsequently, at step 704, at least a portion of the cannula 204 is fastened to the base unit 302. To that end, a fastening unit 304 is used to fasten at least the portion of the cannula 204 to the base unit 302. Particularly, a first sub-unit 318 of the fastening unit 304 is fastened to the base unit 302. The first sub-unit 318 includes a channel on a top surface of the first sub-unit 318. Further, the portion of the cannula 204 is inserted within the channel of the first sub-unit 318. Thereafter, a second sub-unit 320 that is coupled to the first sub-unit 318 is used for clamping the cannula 204 within the channel of the first sub-unit 318. The cannula 204 is clamped in such a way that at least the stylet 206 having the biopsy specimen is projected over a first end of the base unit 302.

Additionally, at step 706, the activator unit 404 of the biopsy collecting device 402 may be attached to the base unit 302. To that end, a holding unit 306 may be used to attach the activator unit 404 to the base unit 302. Particularly, the holding unit 306 may include one or more knobs that are locked with corresponding apertures/rings of the activator unit 404 when the biopsy collecting device is inserted on the needle holder 300. Further, in one embodiment, the activator unit 404 may be actuated for positioning the stylet 206 at a predetermined position/angle in a spectroscopy system 100.

Further, at step 708, the base unit 302 may be coupled to an attaching unit 508 that is used for moving the biopsy collecting device across an illumination path 516. Particularly, the attaching unit 508 may include one or more actuators that are used for moving the needle holder 300 having the biopsy collecting device across the illumination path 516. In one example, the attaching unit 508 may be used for inserting or placing at least the stylet 206 having the biopsy specimen across the illumination path 516.

Figure 8:
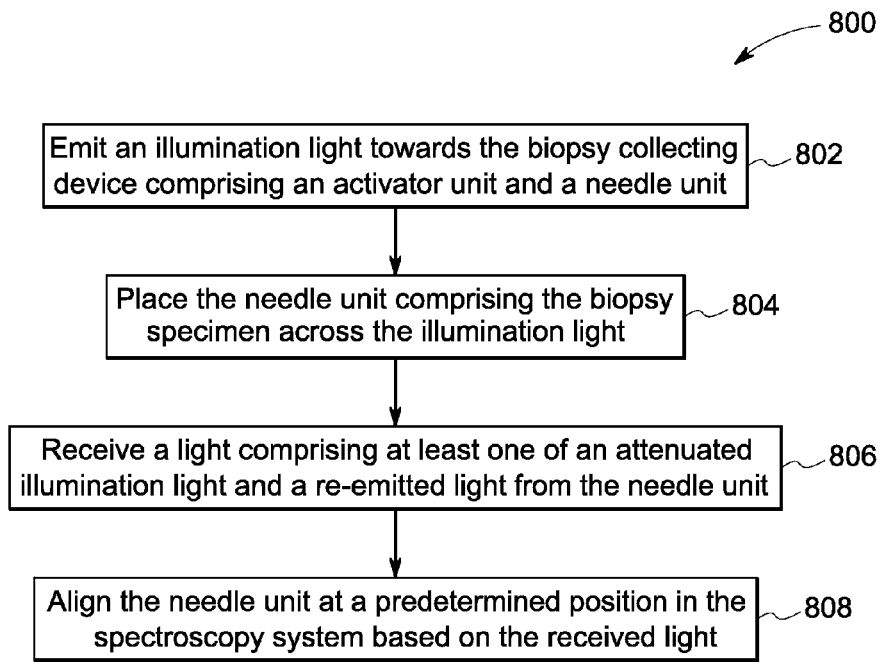
FIG. 8 is a flow chart illustrating a method for auto-aligning a biopsy specimen in a spectroscopy system, in accordance with aspects of the present disclosure.

Referring to FIG. 8, a flow chart illustrating a method for auto-aligning a biopsy specimen in a spectroscopy system, in accordance with aspects of the present disclosure, is depicted. For ease of understanding of the present disclosure, the method is described with reference to the components of FIGS. 1-6. The method begins at step 802, where an illumination light is emitted towards a biopsy collecting device 402. To that end, an illumination subsystem 102 is used for emitting the illumination light. Further, the biopsy collecting device 402 may include an activator unit 404 and a needle unit 406. Also, the needle unit 406 may include a cannula 204 and a stylet 206 having a biopsy specimen.

Subsequently, at step 804, the needle unit 406 having the biopsy specimen is placed across the illumination light. To that end, a fixation subsystem 104 may be used for positioning the needle unit 406 in an illumination path 516 of the illumination light. Particularly, a needle holder 300 having the biopsy collecting device 402 is coupled to the attaching unit 508. Further, the attaching unit 508 is mechanically moved to place the needle unit 406 in the illumination path 516.

Additionally, at step 806, the illumination light that is passing through the needle unit 406 is received by the detection subsystem 106. The received illumination light may be attenuated while passing through the needle unit 406. Particularly, the detecting unit 116 in the detection subsystem 106 may generate an electrical signal corresponding to the received light. Further, the electrical signal is analyzed by a processing unit 118 to estimate transmission losses and/or signal strength in the received light. In one example, the illumination light may be obstructed by a metal portion of the needle unit 406, and the illumination light may not be received by the detection subsystem 106. In such a case, the electrical signal may drop at the processing unit 118. In another example, the illumination light may be passed through the air and there may be no transmission losses in the signal received at the detection subsystem 106. Furthermore, the processing unit 118 determines the current position of the needle unit 406 based on the estimated transmission losses and/or signal strength of the received light.

Further, at step 808, the needle unit 406 is aligned at a predetermined position/angle in the spectroscopy system 100 based on the received light. To that end, the processing unit 118 in the detection subsystem 106 may send a control signal to the fixation subsystem 104 for aligning the needle unit 406 at the predetermined position/angle in the illumination path 516. Particularly, the processing unit 118 may generate the control signal based on the current or determined position of the needle unit 406. Further, the generated control signal is sent to the attaching unit 508 of the fixation subsystem 104 for moving the attaching unit 508 in a forward or backward direction relative to the illumination path 516. More specifically, the attaching unit 508 adjusts the position of the needle holder 300 across the illumination path 516 so that the illumination light is passed through a predetermined location of the biopsy specimen. Also, the needle unit 406 may be moved multiple times for allowing the illumination light to pass through one or more locations of the biopsy specimen. Thus, by employing the current spectroscopy system 100, the biopsy collecting device 402 may be automatically aligned for scanning the biopsy specimen and diagnosing tissue in the biopsy specimen.

Figure 9:
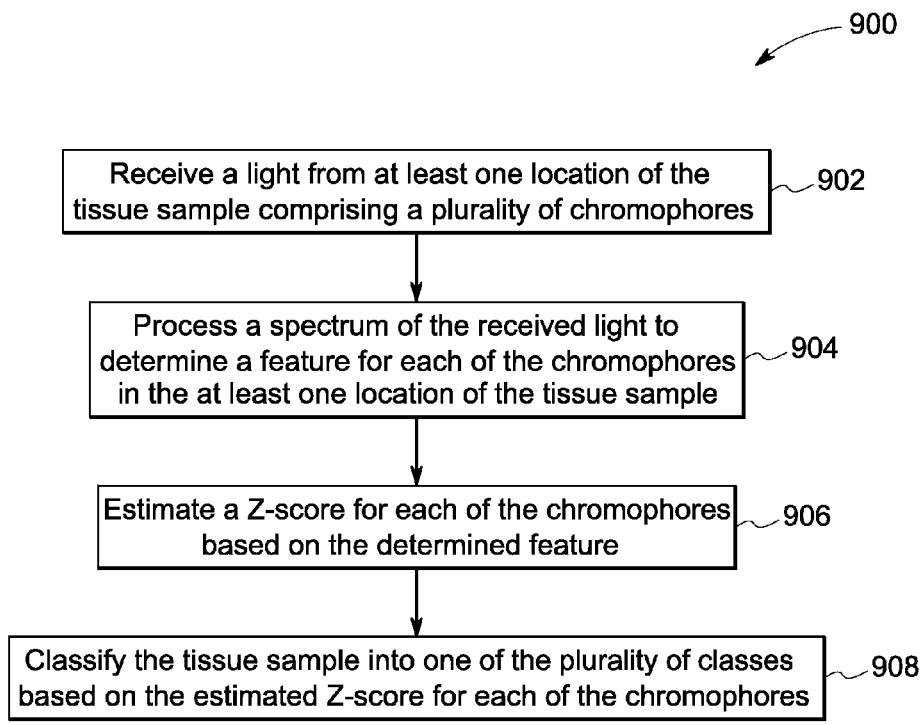
FIG. 9 is a flow chart illustrating a method for characterizing a biopsy specimen in a biopsy collecting device, in accordance with aspects of the present disclosure, is depicted.

Referring to FIG. 9, a flow chart illustrating a method for characterizing a biopsy specimen in a biopsy collecting device, in accordance with aspects of the present disclosure, is depicted. For ease of understanding, the method is described with reference to FIGS. 1-6. The method begins at step 902, where an illumination light that is passed through at least one location of the tissue sample of the biopsy specimen is received by a detection subsystem 600. To that end, a detecting unit 602 in the detection subsystem 600 is used to receive the light 606 that has interacted with the sample. Particularly, the detecting unit 602 may include one or more photo detectors 610 that are used for converting the received light 606 to a corresponding electrical signal 608. Further, the electrical signal 608 may include a spectrum of the received light. This spectrum may further include a plurality of chromophore spectra, wherein each of the chromophore spectra is associated with one of a plurality of chromophores in the at least one location of the tissue sample. Thereafter, the converted electrical signal 608 is transmitted to the processing unit 604 that is communicatively coupled to the detecting unit 602.

Subsequently, at step 904, the spectrum of the received light 606 is processed by a processing unit 604 to determine a feature for each of the chromophores in the at least one location of the tissue sample. Particularly, the spectrum of the received light is processed to determine an optimal linear combination of a pre-stored data that matches with the spectrum of the received light. This determined optimal linear combination of the pre-stored data is further used to estimate the feature for each of the chromophores. In one example, the feature of the chromophore may represent a weight of the chromophore. In one embodiment, the weights may be determined for some of the commonly found or selected chromophores, such as, but not limited to FAD, Beta carotene, fat, lipids, and collagen in the tissue sample. Also, the pre-stored data may include a plurality of library spectra associated with chromophores comprised in one or more pre-determined tissue samples.

In addition, at step 906, a Z-score for each of the chromophores is estimated based on the determined feature. To that end, the processing unit 604 may be used to estimate the Z-score for each of the chromophores. Particularly, the processing unit 604 may determine an error between the spectrum of the received light and the optimal linear combination of the library spectra or pre-stored data. Also, the processing unit 604 may estimate a variance of the determined error and may calculate a co-variance of the library spectra. Further, the processing unit 604 determines the variance of the feature for each of the chromophores based on the variance of the error and the co-variance of the library spectra. Thereafter, the processing unit 604 computes the Z-score for each of the chromophores based on the determined variance of the feature for each of the chromophores.

Additionally, at step 908, the tissue sample is classified based on the estimated Z-score for each of the chromophores. To that end, the processing unit 604 may be used for classifying the tissue samples. More specifically, the processing unit 604 may estimate a calibration parameter based on pre-determined Z-scores of a plurality of pre-classified tissue samples. In one example, the pre-determined Z-scores of normal and abnormal tissue samples are provided to a Generalized Linear Model (GLM) and a value for the calibration parameter is selected in such a way that the probabilistic score for these samples are obtained in a range from '0' to '1'.

Further, this selected calibration parameter is used along with the estimated Z-scores of the actual tissue sample in the biopsy specimen to estimate a probabilistic score for the at least one location of the actual tissue sample. In one example, the selected calibration parameter and the estimated Z-scores of each of the chromophores in the actual tissue sample is provided to the GLM model to obtain the probabilistic score for at least one location of the actual tissue sample. In a similar manner, the probabilistic score for multiple locations of the tissue sample is determined.

Further, the determined probabilistic score for multiple locations of the tissue sample is used to estimate an effective probabilistic score for the whole tissue sample. Thereafter, the effective probabilistic score is used to determine the relative fraction of the tissue sample classified into one of a plurality of classes that includes a normal tissue class and an abnormal tissue class.

The various embodiments of the system and method aid in diagnosing tissue in a biopsy specimen. Also, the amount of diagnostic tissue in an excised biopsy specimen is determined without removing the biopsy specimen from a biopsy needle or a biopsy collecting device. This in turn may reduce the time and cost for examining biopsy of a patient. In addition, exposing the biopsy specimen to air may quickly degrade the tissue sample. Therefore, a fast scan of the biopsy specimen directly in the biopsy needle allows for rapid characterization with minimal impact on the biopsy specimen. Also, characterization in the biopsy needle minimizes the impact on existing clinical workflow. Moreover, the diagnostic tissue in the biopsy specimen may be classified into a normal tissue or an abnormal tissue, which in turn aids in determining the quality, the quantity, and other characteristics of the diagnostic tissue in the biopsy specimen.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method for classifying a tissue sample of a biopsy specimen into one of a plurality of classes, the method comprising:
   receiving a light from at least one location of the tissue sample comprising a plurality of chromophores, wherein the received light comprises at least one of an attenuated illumination light and a re-emitted light;
   processing a spectrum of the received light to determine a feature for each of the chromophores in the at least one location of the tissue sample;
   estimating a Z-score for each of the chromophores based on the determined feature; and
   classifying the tissue sample into one of the plurality of classes based on the estimated Z-score for each of the chromophores.

2. The method of claim 1, wherein processing the spectrum of the received light comprises determining an optimal linear combination of a pre-stored data that matches with the spectrum of the received light, wherein the determined optimal linear combination of the pre-stored data is used to estimate the feature for each of the chromophores.

3. The method of claim 2, wherein the pre-stored data comprises a plurality of library spectra associated with chromophores comprised in one or more pre-determined tissue samples.

4. The method of claim 1, wherein estimating the Z-score for each of the chromophores comprises:
   determining a variance of the feature for each of the chromophores; and
   computing the Z-score for each of the chromophores based on the determined variance of the feature for each of the chromophores.

5. The method of claim 4, wherein determining the variance of the feature for each of the chromophores comprises:
   determining an error between the spectrum of the received light and the optimal linear combination of the library spectra;
   estimating a variance of the determined error;
   calculating a co-variance of the library spectra; and
   determining the variance of the feature for each of the chromophores based on the variance of the determined error and the co-variance of the library spectra.

6. The method of claim 1, wherein the Z-score is calculated using a tissue index ($\beta$) that comprises a plurality of features in a tissue spectrum, wherein the tissue index ($\beta$) is determined using equation:

$$\beta = \frac{1}{T_0} \cdot \prod_j p(\lambda_j),$$

where $T_0$ is a proportionality constant and $p(\lambda_j)$ is the contrast of a particular spectral feature in a region of wavelength $\lambda_j$.

7. The method of claim 6, wherein $p(\lambda_j)$ is defined as a prominence of a spectral peak: $p(\lambda_j)=(T_{max}-T_{min})/(T_{max}+T_{min})$, wherein $T_{max}$ is the maximum of a signal, associated with the received light, measured near the spectral peak of interest and $T_{min}$ is the minimum of the signal, associated with the received light, measured near the spectral peak of interest.

8. The method of claim 6, wherein $p(\lambda_j)$ is defined as an integral of a measured spectrum $T(\lambda)$ over a region of interest:

$$p(\lambda_j) = \int_{\lambda 1}^{\lambda 2} T(\lambda) d\lambda,$$

where $\lambda_j=(\lambda_1+\lambda_2)/2$ is the center of spectral region that extends from $\lambda_1$ to $\lambda_2$.

9. The method of claim 6, wherein $p(\lambda_j)$ is defined as a slope of the spectrum $$p(\lambda_j) = \left|\frac{dT(\lambda)}{d\lambda}\right|^{-1},$$

where $\lambda_j=(\lambda_3+\lambda_4)/2$ is the center of spectral region that extends from $\lambda_3$ to $\lambda_4$.

10. The method of claim 6, where $T_0$ is the normalization constant for the measured spectrum $T(\lambda)$.

11. The method of claim 6, wherein the wavelength $\lambda_j$ is in a range from about 200 nm to 1100 nm.

12. The method of claim 1, wherein classifying the tissue sample comprises:
calculating a tissue index ($\beta$); and
classifying the tissue sample based on a threshold level of the tissue index ($\beta$) between the plurality of classes.

13. The method of claim 1, wherein classifying the tissue sample comprises:
determining a probablistic score for the at least one location of the tissue sample based on the estimated Z-score of each of the chromophores; and
classifying the tissue sample based on the determined probablistic score.

14. The method of claim 13, wherein determining the probablistic score for the at least one location of the tissue sample comprises:
estimating a calibration parameter based on pre-determined Z-scores of a plurality of pre-classified tissue samples; and
computing the probablistic score for the at least one location of the tissue sample based on the calibration parameter and the corresponding Z-score of each of the chromophores.

15. The method of claim 13, wherein determining the probablistic score for the at least one location of the tissue sample comprises calculating the probablistic score for the at least one location of the tissue sample by using a Generalized Linear Model (GLM) algorithm.

16. The method of claim 13, wherein classifying the tissue sample comprises:
computing an effective probablistic score for the tissue sample based on the determined probablistic score of the at least one location of the tissue sample; and
classifying the tissue sample based on the computed effective probablistic score.

17. The method of claim 16, wherein the tissue sample is classified into one of a normal tissue sample and an abnormal tissue sample based on the computed effective probablistic score.

18. A device for classifying a tissue sample of a biopsy specimen into one of a plurality of classes, the device comprising:

a detecting unit configured to receive a light from at least one location of the tissue sample comprising a plurality of chromophores wherein the received light comprises at least one of an attenuated illumination light and a re-emitted light; and
a processing unit coupled to the detecting unit and configured to:
process a spectrum of the received light to determine a feature for each of the chromophores in the at least one location of the tissue sample;
estimate a Z-score for each of the chromophores based on the determined feature; and
classify the tissue sample into one of the plurality of classes based on the estimated Z-score for each of the chromophores.

19. The device of claim 18, wherein the detecting unit comprises at least one detector configured to convert the received light into a corresponding electrical signal.

20. The device of claim 18 further comprising a memory unit coupled to the processing unit and configured to store data having a plurality of library spectra associated with chromophores comprised in one or more pre-identified tissue samples.

21. The device of claim 20, wherein the processing unit is configured to determine an optimal linear combination of the stored data that matches with the spectrum of the received light.

22. The device of claim 18, wherein the processing unit is configured to:
determine a variance of the feature for each of the chromophores; and
compute the Z-score for each of the chromophores based on the determined variance of the feature for each of the chromophores.

23. The device of claim 18, wherein the processing unit is configured to:
determine a probablistic score for the at least one location of the tissue sample based on the estimated Z-score of each of the chromophores; and
classify the tissue sample based on the determined probablistic score.

24. The device of claim 23, wherein the processing unit is configured to:
compute an effective probablistic score for the tissue sample based on the determined probablistic score of the at least one location of the tissue sample; and
classify the tissue sample based on the computed effective probablistic score.

* * * * *